United States Patent
Pyhälahti et al.

(10) Patent No.: US 6,660,898 B1
(45) Date of Patent: Dec. 9, 2003

(54) PROCESS FOR DIMERIZING LIGHT OLEFINS TO PRODUCE A FUEL COMPONENT

(75) Inventors: Antti Pyhälahti, Helsinki (FI); Juhani Aittamaa, Helsinki (FI)

(73) Assignee: Fortum Oil & Gas Oy, Espoo (FI)

( * ) Notice: Subject to any disclaimer, the term of this patent is extended or adjusted under 35 U.S.C. 154(b) by 111 days.

(21) Appl. No.: 09/704,578

(22) Filed: Nov. 3, 2000

(51) Int. Cl.[7] .............. C07C 2/04; C07C 2/24; C07C 1/00
(52) U.S. Cl. ............ 585/510; 585/514; 585/329; 585/639; 585/511
(58) Field of Search ................ 585/510, 514, 585/329, 639, 511

(56) References Cited

U.S. PATENT DOCUMENTS

| | | | |
|---|---|---|---|
| 2,363,300 A | | 11/1944 | Dunstan et al. |
| 4,100,220 A | * | 7/1978 | Bowman et al. ............ 585/515 |
| 4,282,389 A | * | 8/1981 | Droste et al. ............... 568/697 |
| 4,447,668 A | | 5/1984 | Smith, Jr. et al. |
| 5,043,519 A | * | 8/1991 | Orfeo et al. ................ 585/640 |
| 5,227,534 A | * | 7/1993 | Harandi ...................... 568/697 |
| 5,227,564 A | * | 7/1993 | Chen et al. ................. 585/640 |

FOREIGN PATENT DOCUMENTS

| | | |
|---|---|---|
| GB | 522818 | 5/1938 |
| GB | 2325237 | 5/1998 |
| WO | WO 93/13043 | 7/1993 |
| WO | WO9313043 | 7/1993 |
| WO | WO 97/30960 | 8/1997 |
| WO | WO9730960 | 8/1997 |
| WO | WO 00/23402 | 4/2000 |
| WO | WO0023402 | 4/2000 |

* cited by examiner

Primary Examiner—Walter D. Griffin
Assistant Examiner—Tam M. Nguyen
(74) Attorney, Agent, or Firm—Birch, Stewart, Kolasch & Birch, LLP

(57) ABSTRACT

A process for dimerizing light olefinic hydrocarbons in a reaction zone containing a solid acidic catalyst. The process comprises recovering a reaction zone effluent which contains unreacted olefinic hydrocarbons, converting the unreacted olefinic hydrocarbons into an intermediate product in the effluent and separating the intermediate product from the effluent. By decomposing the separated intermediate product the unreacted olefinic hydrocarbons can be recovered and recycled to the reaction zone. By means of the invention, the yield of the product and the lifetime of the catalyst can be improved in a direct dimerization process of light olefins.

6 Claims, 2 Drawing Sheets

PROCESS FOR DIMERIZING LIGHT OLEFINS TO PRODUCE A FUEL COMPONENT

BACKGROUND OF THE INVENTION

1. Field of the Invention

The present invention relates to the preparation of fuel components. In particular the invention relates to a process for producing fuel components comprising dimers of light olefinic hydrocarbons.

2. Description of Related Art

High octane gasoline components can be produced from light olefinic hydrocarbons by dimerization process in which the olefins are dimerized in the presence of an acidic catalyst like an acidic ion exchange resin. Typical feedstocks are $C_4$–$C_6$ isoolefins which can form a tertiary carbocation and give a highly branched dimer which has a better octane number than the less branched molecules. Typical examples of such isoolefins are isobutene and isoamylenes.

In order to produce selectively dimers and to achieve long catalyst life it may become necessary to mix to the feed with sufficient amounts of suitable polar component(s). Examples of such components include water, methanol, tertiary butyl alcohol (TBA), MTBE and similar oxygenates. According to a particularly interesting process, $C_4$- and $C_5$-olefins are dimerized in the presence of alcohol or another oxygenate in a reaction sequence comprising at least one distillation zone and at least one reaction zone. The reaction is carried out at conditions in which at least part of the olefins dimerize. The distillation zone is arranged after the reaction zone, and a flow comprising an oxygenate, such as alcohol or water or the product(s) of reaction(s) between alcohol or water and the olefin(s) present in the feed, or a mixture of any or all of these is circulated from the distillation zone back to the dimerization. At least one circulation flow is withdrawn from the side of at least one distillation column. The molar ratio of alcohol or other oxygenate and isobutene is adjusted to be small during the reaction, thus maintaining the rate of dimerization high.

We have found that, to some extent, the polar component also reduces catalyst activity. This effect is not too significant when the concentration of the component to be dimerized is high, but if very high conversion is required, and the whole conversion is made in a simple once-through mode, the reaction rate can be very low near the outlet.

There are some possibilities of solving the problem. One option is to split up the reactor train in two parts and having a separation stage introduced between the reactors so as to reduce oxygenate level of the reaction mixture before it is fed into the secondary reactor train. A process configuration of this kind is depicted in FIG. 1 and it solves the reaction rate problem at the cost of lower selectivity and reduced catalyst life time in the secondary reactor train.

An alternative solution would be to replace the secondary reactor(s) of the previous embodiment with equipment in which the remaining reactants can be recovered as such and returned back to the primary reactors instead of forcing the dimerization reaction to completion by very severe reaction conditions. FIG. 2 depicts the block scheme of such a plant.

The arrangement of FIG. 2 has many advantages over the arrangement of FIG. 1, such as better product quality and longer catalyst life because the secondary stage is eliminated. However, a problem remaining with the embodiments of FIG. 2 is how to separate the reactants from the remaining inert hydrocarbons. The traditional method of separating components from hydrocarbon mixture is distillation. Technically distillation can be applied here, too, but because usually inert components and the reactants have boiling points very near to each other (e.g., feed contains mostly isobutane and isobutene), the column would be a typical superfractionator with very large dimensions and high energy consumption.

SUMMARY OF THE INVENTION

It is an aim of the present invention to eliminate the problems of the prior art and to provide a novel process for separating and circulating unreacted reactants during the production of fuel components based on dimerization of light olefinic feedstocks.

The present invention is based on the idea of recovering the unreacted reactant from the reactor effluent by using a reversible chemical reaction, in which the reactant is first converted to an intermediate product which can easily be separated from the mixture and this intermediate product is then decomposed back to the reactant and returned to the primary reactor feed.

More specifically, the present invention is mainly characterized by what is stated in the characterizing part of claim 1.

Considerable advantages are obtained by the invention. Thus, by combining the dimerization process with chemical recovery of the light olefin reactant, the yield and catalyst lifetime problems of the direct dimerization process can be solved.

DETAILED DESCRIPTION OF THE INVENTION

Figure 1:
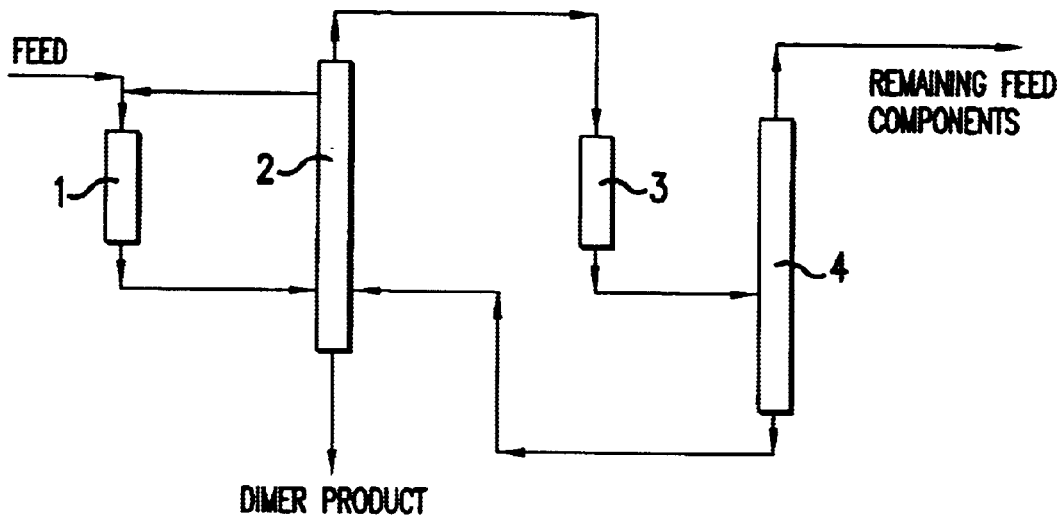
FIG. 1 is a block diagram of a process for dimerization of light olefins.

For the purposes of the present invention, the "separation unit" typically designates a distillation system comprising one or more distillation columns. The columns are preferably connected in series. The feed plate can be selected for each column to be most advantageous in view of the overall process. Likewise, the plates for sidedraw of flows to be recovered or circulated can be selected individually for each column. The distillation column can be any column suitable for distillation, such as a packed column, or one provided with valve, sieve or bubble-cap trays.

A "reaction section" or "reaction zone" comprises at least one, typically two or three, reactor(s). The reactor can be, e.g., a tubular reactor with multiple pipes, wherein the pipes are filled with catalyst. Other possibilities include a simple tubular reactor, a boiler reactor, a packed bed reactor and a fluidized bed reactor. The reactor used is preferably such in which the catalyst is placed in more than one layer and cooling is introduced between the layers. Preferably at least one of the reactors has a cooling system. For example, the pipes of the tubular reactor with multiple pipes can be cooled. Another example of a suitable reactor is a combination of a fixed bed reactor and a cooler, in which part of the reactor effluent can be circulated back to the reactor via the cooler. The operating pressure of the reactors depends on the type of the reactor and on the composition of the feed, typically it is desired to keep the reaction mixture in liquid phase.

The term "oxygenate" designates a compound containing oxygen. Typically, the oxygenates used in the present invention are primary, secondary or tertiary alcohols or ethers, or water.

"Isooctene" and "diisobutene" are both products of isobutene dimerization. Thus they can be used interchangeably to designate 2,4,4-trimethyl-1-pentene and 2,4,4-trimethyl-2-pentene or a mixture thereof.

"Reaction mixture" or "reaction effluent" contains the desired product of the dimerization reaction in the reaction zone. With only $C_4$-olefins or only $C_5$-olefins are fed to the process, it is clear that the resulting product of the mutual reactions of the olefins yield dimers. However, when both $C_4$- and $C_5$-olefins are present in the feed, in addition to dimerization, also reactions between $C_4$-olefins and $C_5$-olefins yielding $C_9$-olefins can occur. The word "dimer" is also used for the reaction products in the specification for reasons of simplicity, but it is to be understood that when both $C_4$- and $C_5$-olefins are present in the feed, the reaction mixture typically contains also some amount of the $C_9$-olefins.

The feed of the process according to the present invention is a hydrocarbon mixture containing olefins. The feed comprises olefins to be dimerized at least 10 wt-%, preferably at least approximately 20 wt-%. As already described, the olefins are selected from the group of linear 1- or 2-butene, isobutene and linear or branched $C_5$-olefins. Alternatively, the feed can comprise a mixture of any or every of the olefins listed above. Typically, the feed comprises dimerizable components; either $C_4$-olefins, preferably isobutene, whereby iso-octene is produced, or $C_5$-olefins, whereby substituted $C_{10}$-olefins are produced. It is clear that both $C_4$- and $C_5$-olefins can be present in the feed, whereby a great variety of products is produced. The composition of the product flow is discussed later.

According to the first preferred embodiment, in which $C_4$-hydrocarbons are dimerized, the hydrocarbon mixture in the feed comprises at least 10 wt-%, preferably at least approximately 20 wt-% isobutene. The feed can consist of pure isobutene, but in practice, the feedstock readily available comprises $C_4$-based hydrocarbon fractions from oil refining. Preferably, the feed comprises a fraction obtained from isobutane dehydrogenation, when the feed comprises mainly isobutene and isobutane and possibly small amounts of $C_3$- and $C_5$-hydrocarbons. Typically the feed then comprises 40–60 wt-% of isobutene and 60–40 wt-% isobutane, usually there is 5–20% less isobutene present than isobutane. Thus, the ratio of isobutene to isobutane is approximately 4:6 . . . 5:5.5. As an example of an isobutane dehydrogenation fraction, the following can be presented: 45 wt-% isobutene, 50 wt-% isobutane and other inert $C_4$-hydrocarbons and approximately 5 wt-% of $C_3$-, $C_5$- and heavier hydrocarbons altogether.

Due to the high isobutene content in the flow from the isobutane dehydrogenation the amounts of inert hydrocarbons in the recycling flows remain relatively small. The dehydrogenation fraction is very suitable for producing a product with a very high content of the dimerized isobutene.

The feed for producing iso-octene is also possible to select from the group containing $C_4$-fractions of FCC, TCC, DCC and RCC or from the $C_4$-fraction after the removal of butadiene, also called Raffinate 1 of an ethyl unit. Of these FCC, RCC, TCC and Raffinate 1 are preferred, since the hydrocarbon fractions can be used as such, possibly after removing the heavier ($C_{8+}$) fractions. Raffinate 1 is typically composed of approximately 50 wt-% isobutene, approximately 25 wt-% linear butenes and approximately 25 wt-% paraffins. The product from the FCC is typically composed of 10–50, in particular 10–30 wt-% isobutene, 20–70 wt-% 1- and 2-butene and approximately 5–40 wt-% butane. As an example of a typical FCC-mixture, the following can be presented: approximately 30 wt-% isobutene, approximately 17 wt-% 1-butene, approximately 33 wt-% 2-butene and approximately 20 wt-% butane.

Also isobutene prepared from chemicals can be used as feed.

If the present invention is used for converting linear butenes, the linear butenes are preferably selectively isomerized to 2-butene as completely as possible. In this case, it is preferable to add a separate side reactor circulation to the process configuration. The temperature in this reactor is preferably higher than in the prereactor or circulation reactor in order to increase the conversion of dimerization.

FCC and corresponding hydrocarbon flows are suitable to use, e.g., in cases where the conventional MTBE unit is used to produce a product mixture comprising iso-octene and MTBE.

According to the second preferred embodiment of the invention, in which $C_5$-olefins are dimerized, the feed comprises olefins selected from the group of linear and branched $C_5$-olefins, or a mixture thereof. Thus, the olefins typically present in the feed comprise linear pentene, 2-methyl-1-butene, 2-methyl-2-butene, 3-methyl-1-butene or 2-ethylpropene. Also some amounts of $C_6$-olefins, typically at least 5 wt-% can be present in the feed.

Typically, the feed in the second preferred embodiment is FCC gasoline, light FCC gasoline, pyrolysis-$C_5$-gasoline, TCC gasoline, RCC gasoline and Coker gasoline, typically the $C_5$-fraction of FCC gasoline, and can thus comprise also some $C_6$-olefins. Advantageously, the FCC fraction is fractionated to obtain as pure $C_5$-olefin fraction as possible where other $C_5$-hydrocarbons are present in less than 15 wt-%, preferably less than 5 wt-%. It is possible to use a fraction comprising also $C_6$-olefins. Typically, the feed then comprises 20 to 60 wt-%, in particular 30 to 50 wt-% $C_5$-olefins, 10 to 30 wt-%, in particular 15 to 25 wt-% $C_6$-olefins and 15 wt-% or less parafinic hydrocarbons pentanes.

According to the third preferred embodiment, the feed comprises both $C_4$- and $C_5$-olefins. In this case, the feed is typically selected from the group comprising FCC, TCC, DCC and RCC or from the $C_4$-fraction after the removal of butadiene, also called Raffinate 1 of an ethylene unit, FCC gasoline, light FCC gasoline, pyrolysis-$C_5$-gasoline, TCC gasoline, RCC gasoline and Coker gasoline. A fraction readily available comprises $C_4$ and $C_5$ fractions from FCC. Advantageously, a fraction comprising at least 10 wt-%, preferably at least 15 wt-% $C_4$-olefins and at least 10 wt-%, preferably at least 15 wt-% $C_5$-olefins is used. Typically the amounts of $C_4$-olefins and $C_5$-olefins are approximately equal, although a slight dominance of $C_4$-olefins in the fraction is also usual.

In addition to the hydrocarbon, an oxygen-containing compound (an oxygenate), such as alcohol, is fed into the process in order to slow down the oligomerization reactions of the olefin and to decrease the catalyst poisoning. Instead of alcohol, another possibility is to feed to the process a compound that will form alcohol. The use of oxygenate increases the dimer selectivity whereby the portion of trimers and tetramers of the olefin oligomers decreases. Thus, the fraction of dimers of the formed olefin oligomers is typically at least 80 wt-%. The oxygen containing (and alcohol forming) compound can be fed together with the fresh olefin feed, or it can be fed together with the circulation flow, or directly to the reaction zone.

The present invention aims at providing an advantageous way of recovering and recycling unreacted light olefins from the reactor effluent. As discussed above, a conventional dimerization plant can be modified by splitting the reactor train up in two parts with an intermediate separation stage between the reactor stages. FIG. 1 shows, in the form of a block diagram, the process scheme of such a modified dimerization plant. The plant comprises primary reactors 1 in which the concentration of oxygenate is high. The effluent of the primary reactor section is conducted to primary separation, i.e. a distillation column 2. A sideway is recirculated to the feed of the primary reactor, whereas the overhead is conducted to a secondary reaction section 3. The effluent of the secondary reaction section is conducted to secondary separation 4. The bottoms product of the secondary reaction section 4 is recirculated to the primary separation unit 2 whereas the unreacted feed components are removed in the form of the overhead product.

Figure 2:
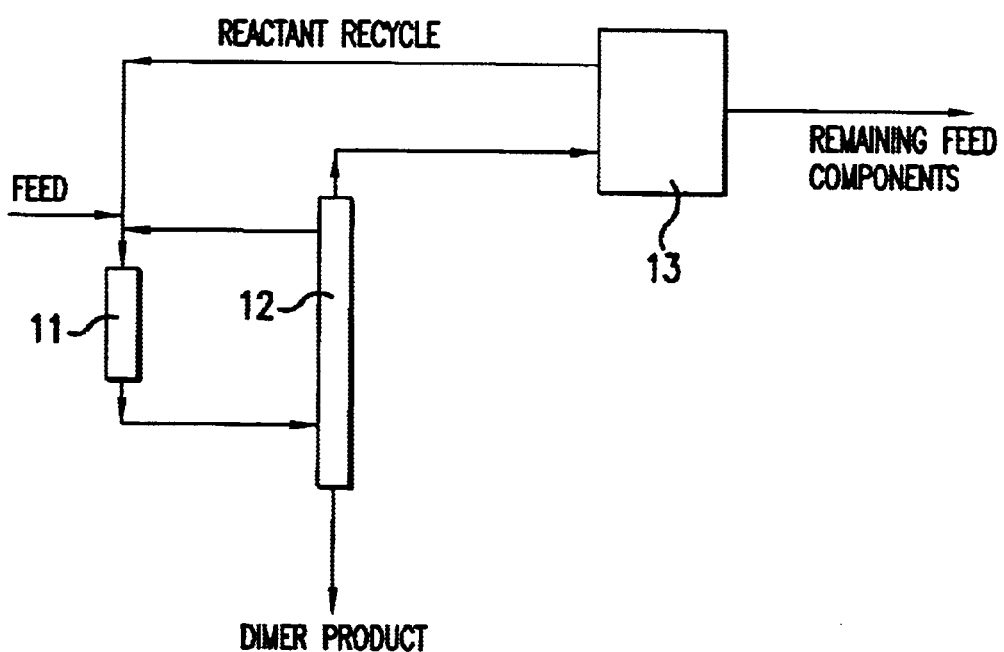
FIG. 2 is a block diagram of an isoolefin dimerization plant with reactant recovery.

Another option would be to replace the secondary reactor with separate recovery unit, as depicted in FIG. 2. The plant comprises primary reactors 11. The effluent of the primary reactor section is conducted to primary separation, i.e. a distillation column 12. A sidedraw is recirculated to the feed of the primary reactor, whereas the overhead is conducted to a reactant recovery section 13. The reactants separated are recycled to the feed of the primary reactor section, whereas the unreacted feed components are removed in the form of an effluent.

The present invention is, however, based on a different approach in which the reactor effluent, optionally after separation of the dimer product, is subjected to a reaction in which an intermediate product is formed from the unreacted light olefins. In particular, the invention is based on the idea of using a reversible reaction, whereby the reactant is first converted to an intermediate product which can be separated easily from the mixture and then this intermediate product is decomposed back to the reactant and returned to the primary reactor feed.

Figure 3:
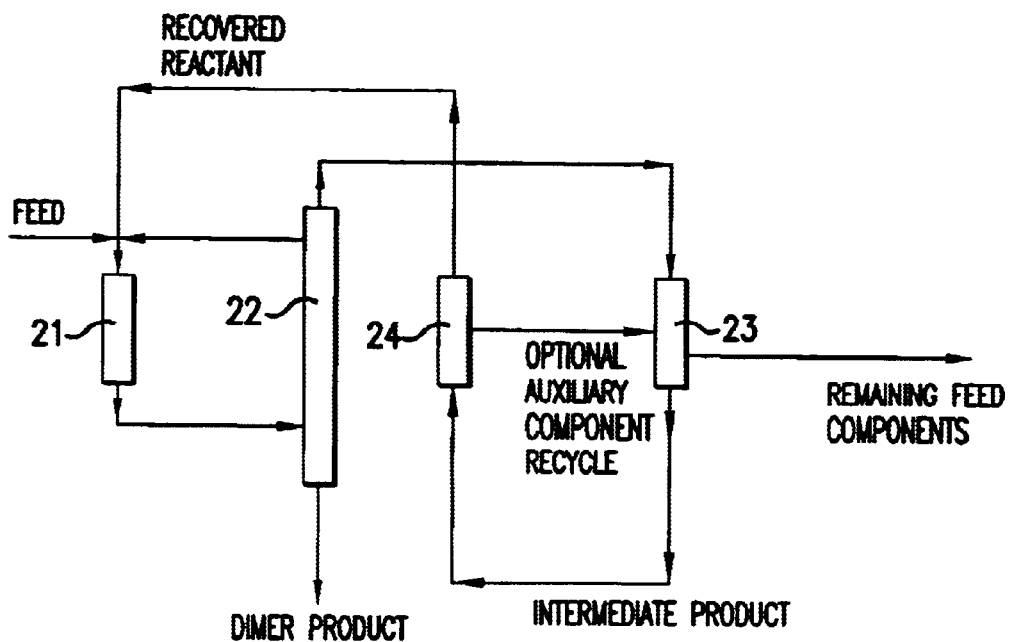
FIG. 3 is a block diagram of a high conversion light olefin dimerization plant using chemical recovery of the reactants.

The general principles of the process according to the invention are depicted in FIG. 3, which shows the block diagram of a high conversion light olefin dimerization plant using chemical recovery of the reactants. According to the invention a hydrocarbon feed containing olefins, in particular isoolefins, is contacted with a catalyst together with alcohol or other oxygenate in a first reaction zone 21 at conditions in which at least a part of the olefins is dimerized. In case where the olefin feed comprises both $C_4$- and $C_5$-olefins, also reactions between different olefins occur, thus forming $C_9$-olefins. In addition also small amounts of other oligomers, such as trimers or tetramers are formed in the reaction.

In the dimerization, an acidic catalyst is used. Preferably, ion-exchange resins are used, for example such as are used for etherification. As catalysts can, however, be used zeolites and other inorganic catalysts. Thus, the resin can comprise sulphonic acid groups and it can be prepared by polymerizing or copolymerizing aromatic vinyl compounds and, thereafter, sulphonating. As examples of aromatic vinyl compounds the following may be mentioned: styrene, vinyl toluene, vinyl naphthalene, vinyl ethyl benzene, methyl styrene, vinyl chlorobenzene, and vinyl xylene. An acidic ion-exchange resin contains typically approximately 1.3 . . . 1.9, even up to 2 sulphonic acid groups per an aromatic group. Preferred resins are those based on copolymers of aromatic monovinyl compounds and aromatic polyvinyl, in particular divinyl, compounds, in which the concentration of polyvinylbenzene is approximately 1 . . . 20 wt-% of the copolymer. The particle size of the ion-exchange resin is preferably approximately 0.15 . . . 1 mm.

In addition to the resins already described, also perfluorosulphonic acid resins consisting of copolymers of sulphonylfluorovinyl ethyl and fluorocarbon compounds can be used.

Various suitable ion-exchange resins are commercially available, an example of these is Amberlyst 15.

The concentration of the catalyst is typically 0.01–20%, preferably approximately 0.1–10% of the weight of the liquid mixture to be handled.

The temperature of the reaction zone is typically 50–120° C. The upper level of the temperature range is set by the heat-resistance properties of the catalyst. The reaction can very well be carried out at temperatures higher than 120° C., for example up to 160° C. or even higher. The formation of the dimers can be enhanced by increasing the temperature during the reaction. On the other hand, a lower temperature favours the formation of ether.

From the primary reactors 21 the reaction effluent is conducted to a primary separation section comprising, e.g., a distillation column 22. As is shown in FIGS. 1 and 2, a sidedraw comprising alcohol, other oxygenate and/or the reaction product is circulated from the primary separation zone back to the reaction zone. With the help of the sidedraw the conversion of the olefin and the production of dimerized product is increased. It is to be understood, that although the following description refers to a sideflow in singular, which is the typical configuration, it is also possible to withdraw two or more sideflows containing oxygenate and circulate all those flows back to dimerization.

The distillation column 22 bottoms comprise the dimer product, whereas the overhead which mainly comprises unreacted olefins and inert hydrocarbon (alkanes) is conducted to an intermediate product formation section 23. In this reaction section the unreacted olefins are converted into an intermediate product which can be separated from the other components of the feed. Preferably the intermediate product is formed by means of a reversible reaction by contacting the light olefins with an auxiliary component which is fed into the secondary reaction section. The secondary reaction section can comprise a reactive distillation column or a reactive absorption column, wherein the reaction takes place optionally in the presence of a catalyst. The reversible reaction can be any equilibrium reaction, in which the balance is on the left-hand or right-hand side, respectively, depending on process conditions. In the intermediate product formation section the reaction conditions are such that the balance is on the product side of the reversible reaction. The inert components of the process feed are separated from the intermediate product and separately recovered. The intermediate product is recovered as reactor effluent and conducted to a reaction unit 24 for intermediate product decomposition. The process equipment of the intermediate product decomposition unit 24 can be similar to that used for the formation of the intermediate product 23. As a result of the decomposition of the intermediate product, the auxiliary component is recovered and it can be recycled to the formation unit. The released olefins are recovered and recycled to the feed of the dimerization reactor section 21.

Assuming that the main components of the feed to the process are isobutene and isobutane and water or tertiary butyl alcohol (TBA) is used the selectivity improving oxygenate, a particularly preferred embodiment of carrying out the formation of the intermediate product is reversible TBA formation from water and isobutene. In this embodiment there is no need to introduce to the process any component which was not already present in the system. The intermediate component is TBA and the reaction taking place is:

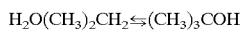

Figure 4:
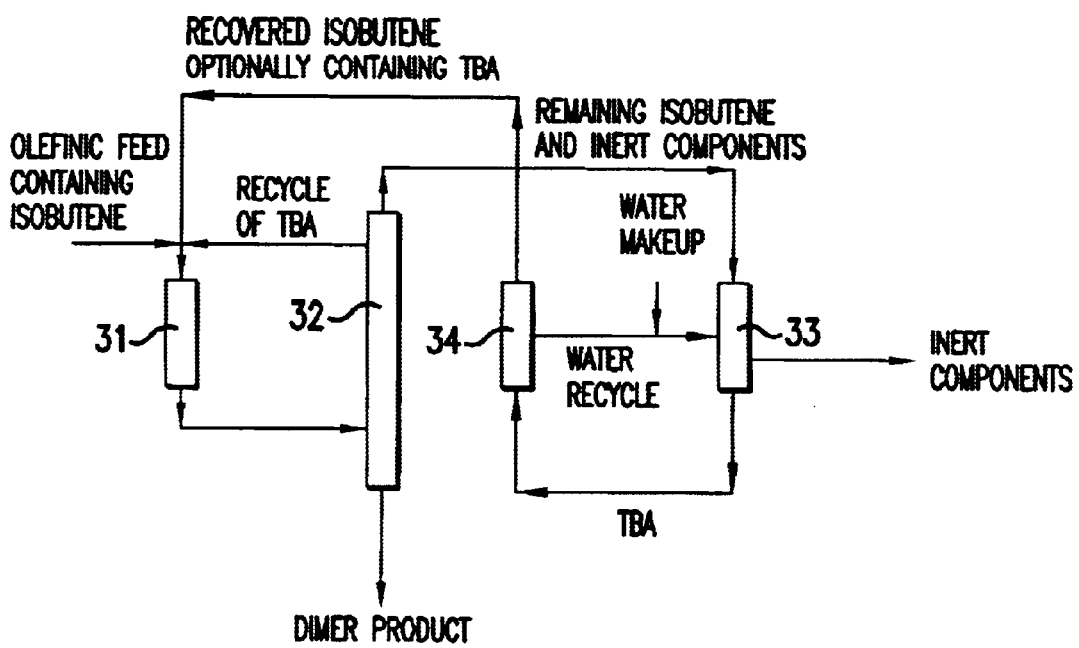
FIG. 4 is a block diagram of a process similar to that depicted in FIG. 3 in which TBA is used for conversion of the unreacted reactants.

FIG. 4 presents the block diagram of such process. As in the embodiment of FIG. 3, the hydrocarbon feed containing olefins, in particular isoolefins, is contacted with a catalyst together with alcohol or other oxygenate in a first reaction zone 31 at conditions in which at least a part of the olefins is dimerized. The reactor contain a high oxygenate level. From the primary reactors 31 the reaction effluent is conducted to a primary separation section comprising, e.g., a distillation column 32. By means of the sidedraw TBA present in the dimerization reactor effluent is recycled to the reactors 31 from the column 32. The overhead of the column is conducted to TBA formation 33.

The details of reaction equipment needed for converting isobutene and water to TBA and decomposing TBA back to its constituents are known technology as such. Reactive distillation column with cationic ion exchange resin packing or various combinations of reactors and distillation columns can be utilized.

The TBA formation can be carried out by contacting water and isobutene in a concurrently or counter-currently operating reactor. The isobutene can be fed into the TBA formation section in liquid or gas state. According to an interesting embodiment, the overhead of the separation section 32 is not condensed but fed as such in gas phase into the following unit. In the case of gas phase feed of the isobutene, counter-current operation of the TBA formation section 33 is preferred, whereby the gas is entered from below and water from above.

It is desirable, in view of the equilibrium reaction between water and isobutene that the reaction mixture is dilute in respect to the isobutene. Typically, the concentration of isobutene in less than 10 mol-%, preferably less than about 5 mol-%, typically on the order of about 4 to 0.1 mol-%.

The reaction conditions can vary depending on the concentration of the various components, the catalyst used etc. However, generally it is preferred to operate the TBA formation process at overpressure and at an elevated temperature, i.e. a temperature higher than room temperature. Pressures (absolute) in the range of about 2 to 50 bar, preferably about 2.5 to 20 bar, in particular about 3 to 15 bar, are generally preferred. The temperatures are typically in the range of about 30 to 300° C., in particular about 50 to 200° C. It is preferred to operate at a temperature which makes it possible to separate the inert hydrocarbon, such as isobutane, from the reaction effluent in gaseous form.

From the TBA formation the intermediate product is conducted to TBA decomposition 34. The equipment can be similar to that used for TBA formation. The operating conditions are, however, such that the balance of the TBA formation reaction is on the left-hand side. Thus, the TBA—water mixture is preferably concentrated in respect of TBA (TBA concentration in excess of 50 mol-%, preferably in excess of 70 mol-%). Preferably the TBA formation unit is operated in such a way that the TBA—water mixture can be fed into the decomposition step as an azeotropic mixture. Generally the temperature and pressure can be the same as for TBA formation, although somewhat lower pressures (slight overpressures of 1.1 to 5 bar) are preferred.

The water released from the decomposing TBA is recycled and combined with fresh feed if necessary before it is introduced into the TBA formation unit. The isobutene released from the TBA is recovered and recycled to dimerization.

Both TBA formation and TBA decomposition can be carried out in the presence of a catalyst of the kind disclosed above in connection with dimerization.

TBA formation is described in, e.g., the following article in more detail:

Velo, E., Puigjaner, L., Recasens, F., Inhibition by product in the liquid-phase hydration of isobutene to tert-butyl alcohol: Kinetics and equilibrium studies, Ind. Eng.Chem.Res. 1988, 27, 2224–2231.

TBA decomposition is disclosed in, e.g., the following article:

Abella, L. C., Gaspillo, D., Maeda, M., Gotto, S., Kinetic Study on the dehydration of tert-butyl alcohol catalyzed by ion exchange resins, Int. J. Chem Kinet 1999, 31, 854–859.

If should be noted that there are other alternatives to TBA formation. Thus, it is possible to use the MTBE formation reaction for recovering the isobutene. It is analogous to using TBA formation, but if no MTBE is allowed in the dimer product, both methanol and MTBE must be separated very carefully from the recycled isobutene. In the case of TBA, some TBA in the recycle is even useful because it provides the oxygenate makeup needed by the dimerization step.

By combining the dimerization process and chemical recovery of the light olefin reactant, the yield and catalyst lifetime problems of the direct dimerization process can be solved.

What we claim is:

1. A process for dimerizing light olefinic hydrocarbons comprising the steps of:

feeding a hydrocarbon feedstock comprising light olefins into a first reaction zone containing a solid acidic catalyst;

feeding an oxygenate into the first reaction zone;

contacting the hydrocarbon feedstock with the solid acidic catalyst in the presence of the oxygenate to dimerize light olefins of the feedstock into the corresponding dimers;

recovering the dimers and unreacted light olefins from the first reaction zone;

converting the unreacted light olefins into an intermediate product in the presence of the same or a different oxygenate in a recovery section, wherein said intermediate product is an alcohol or an ether formed by the reversible reaction of the light olefins and the oxygenate;

separating the intermediate product from the unreacted light olefins;

decomposing the intermediate product to form the corresponding light olefins; and recycling the formed light olefins to the first reaction zone.

2. The process according to claim 1, wherein the light olefinic hydrocarbon to be dimerized is isobutene;

the oxygenate used for controlling the reaction selectivity is water or tertiary butyl alcohol or a mixture thereof, and the reaction which takes place in the recovery section is the formation of tertiary butyl alcohol from isobutene and water.

3. The process according to claim 1, wherein the light olefinic hydrocarbon to be dimerized is isobutene, the oxygenate for controlling the reaction selectivity is water or tertiary butyl alcohol or a mixture thereof, and the reaction taking place in the recovery section is the formation of methyl tertiary butyl ether from isobutene and methanol.

4. The process according to claim 1, wherein the light olefinic hydrocarbon to be dimerized is isoamylene or a mixture of isoamylene and isobutene;

the oxygenate for controlling the reaction selectivity is a mixture of water, tertiary butyl alcohol or tertiary amyl alcohol or a mixture of them; and the reaction taking place in the recovery section is the formation of tertiary amyl alcohol and tertiary butyl alcohol.

5. A process for dimerizing light olefinic hydrocarbons in a reaction zone containing a solid acidic catalyst, comprising recovering a reaction effluent which contains unreacted olefinic hydrocarbons and dimers, converting the unreacted olefinic hydrocarbons in the presence of an oxygenate into an intermediate product in the effluent, separating the intermediate product from the effluent, decomposing the separated intermediate product to form light olefinic hydrocarbons and recycling the light olefinic hydrocarbons to the reaction zone.

6. The process according to claim 5, wherein the dimer is first separated from reaction zone effluent before it is subjected to conversion of the unreacted olefinic hydrocarbons.

* * * * *